(12) United States Patent
Keenan et al.

(10) Patent No.: US 11,241,568 B2
(45) Date of Patent: Feb. 8, 2022

(54) DISTAL BEARING SUPPORT

(71) Applicant: TC1 LLC, Pleasanton, CA (US)

(72) Inventors: Richard L. Keenan, Livermore, CA (US); Keif M. Fitzgerald, San Jose, CA (US)

(73) Assignee: TC1 LLC, Pleasanton, CA (US)

( * ) Notice: Subject to any disclaimer, the term of this patent is extended or adjusted under 35 U.S.C. 154(b) by 539 days.

(21) Appl. No.: 16/151,651

(22) Filed: Oct. 4, 2018

(65) Prior Publication Data

US 2019/0030228 A1 Jan. 31, 2019

Related U.S. Application Data

(63) Continuation of application No. 15/266,864, filed on Sep. 15, 2016, now Pat. No. 10,117,980, which is a (Continued)

(51) Int. Cl.
| | |
|---|---|
| *A61M 60/00* | (2021.01) |
| *A61M 60/148* | (2021.01) |
| *A61M 60/205* | (2021.01) |
| *A61M 60/818* | (2021.01) |
| *A61M 60/135* | (2021.01) |

(Continued)

(52) U.S. Cl.
CPC .......... *A61M 60/00* (2021.01); *A61M 60/148* (2021.01); *A61M 60/205* (2021.01); *A61M 60/818* (2021.01); *A61M 60/135* (2021.01); *A61M 60/414* (2021.01); *A61M 60/824* (2021.01); *F04D 1/00* (2013.01); *F04D 25/06* (2013.01)

(58) Field of Classification Search
CPC .......... F04D 1/00; F04D 25/06; A61M 60/00; A61M 60/205; A61M 60/135; A61M 60/824; A61M 60/414; A61F 2002/9505
See application file for complete search history.

(56) References Cited

U.S. PATENT DOCUMENTS

| | | |
|---|---|---|
| 5,964,694 A | 10/1999 | Siess et al. |
| 6,468,298 B1 | 10/2002 | Pelton |

(Continued)

FOREIGN PATENT DOCUMENTS

| | | |
|---|---|---|
| WO | 2010127871 A1 | 11/2010 |
| WO | 2011089022 A1 | 7/2011 |

OTHER PUBLICATIONS

Extended European Search Report, dated Aug. 31, 2020, for related EP patent application EP 20176135.0 (7 pages).

*Primary Examiner* — Ariana Zimbouski
(74) *Attorney, Agent, or Firm* — Armstrong Teasdale LLP

(57) ABSTRACT

In various embodiments, a catheter pump is disclosed herein. The catheter pump can include an elongated catheter body having a distal portion including an expandable cannula having an inlet and an outlet. The expandable cannula can have a delivery profile and an operational profile larger than the delivery profile. An impeller assembly can include an impeller shaft, and an impeller body can include one or more blades. The impeller blades can draw blood into the cannula when rotated. Further, an expandable support can have a mounting portion disposed on the impeller shaft distal of the impeller body and a cannula contact portion for reducing a change in tip gap due to bending of the cannula. The cannula contact portion can be disposed distal of the mounting portion.

20 Claims, 10 Drawing Sheets

Related U.S. Application Data continuation of application No. 13/802,556, filed on Mar. 13, 2013, now Pat. No. 9,446,179.

(60) Provisional application No. 61/646,755, filed on May 14, 2012.

(51) Int. Cl.
*A61M 60/414* (2021.01)
*A61M 60/824* (2021.01)
*F04D 1/00* (2006.01)
*F04D 25/06* (2006.01)

(56) References Cited

U.S. PATENT DOCUMENTS

| | | |
|---|---|---|
| 8,690,749 B1 | 4/2014 | Nunez |
| 2011/0004046 A1 | 1/2011 | Campbell et al. |

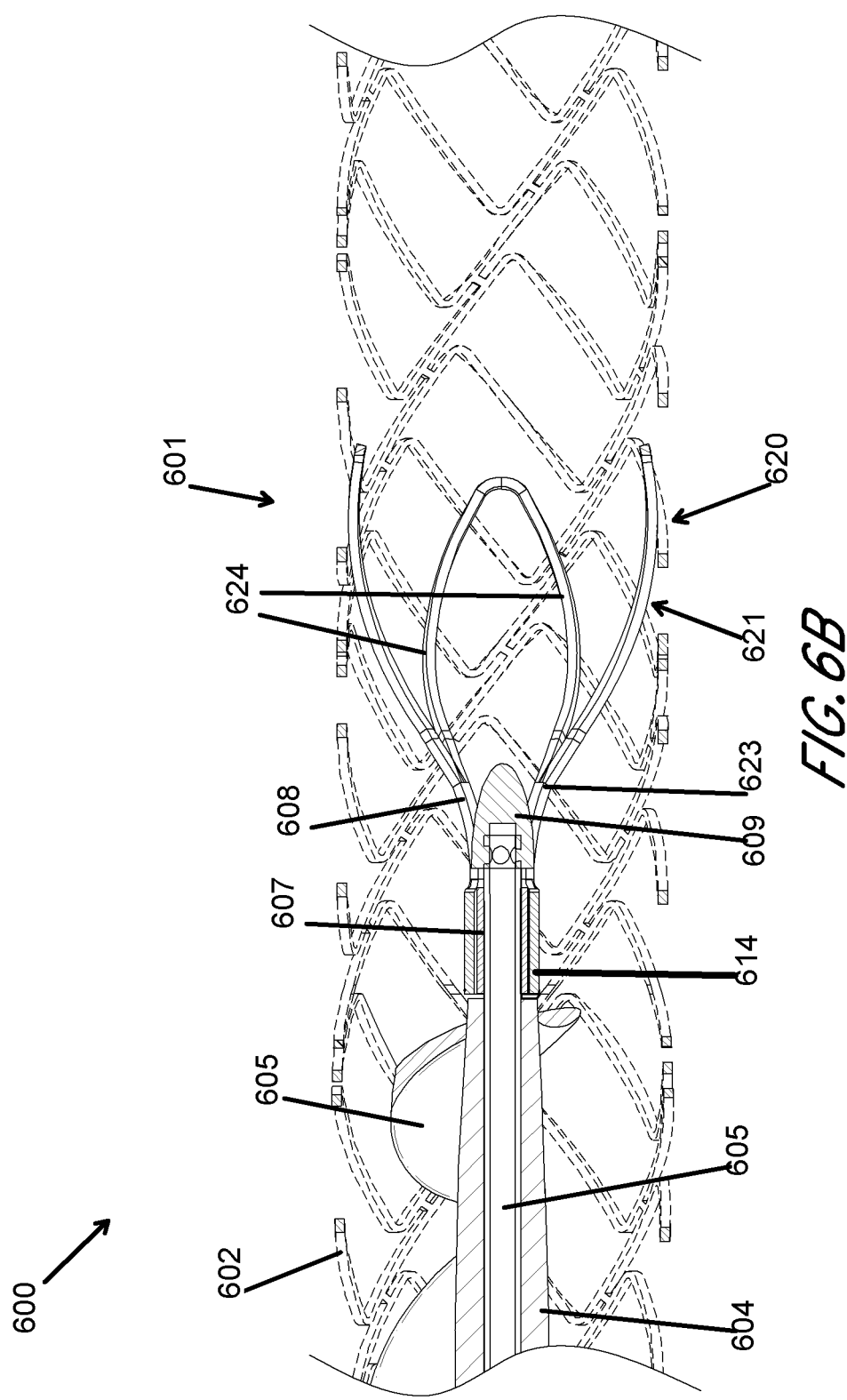

DISTAL BEARING SUPPORT

INCORPORATION BY REFERENCE TO ANY PRIORITY APPLICATIONS

This application is a continuation of U.S. patent application Ser. No. 15/266,864 filed on Sep. 15, 2016, now issued U.S. Pat. No. 10,117,980, which is a continuation of U.S. patent application Ser. No. 13/802,556, filed Mar. 13, 2013, now issued U.S. Pat. No. 9,446,179, which claims priority to U.S. Provisional Patent Application No. 61/646,755, filed May 14, 2012. Any and all applications for which a foreign or domestic priority claim is identified in the Application Data Sheet as filed with the present application, including U.S. application Ser. No. 15/266,864, U.S. application Ser. No. 13/802,556, and U.S. Application No. 61/646,755, are hereby incorporated by reference under 37 CFR § 1.57 in their entirety and for all purposes.

BACKGROUND OF THE INVENTION

Field of the Invention

This application is directed to pumps for mechanical circulatory support of a heart. In particular, this application is directed to support structures for an impeller assembly that can be used in a catheter pump.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15 FR or 12 FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow while minimizing the likelihood of hemolysis at high rotational speeds. These and other problems are overcome by the inventions described herein.

Further, there is a need for providing an operative device of the pump capable of pumping blood at high flow rates while reducing the risk of hemolysis at the operative device. For example, when an impeller assembly is provided at the operative device, the high rate of rotation of the impeller may cause hemolysis, as blood flows past the high-speed impeller. Accordingly, there is a need for reducing the risk of hemolysis at the operative device of the pump, particularly when movable components are disposed at the operative device.

SUMMARY OF THE INVENTION

There is an urgent need for a pumping device that can be inserted percutaneously and also provide full cardiac rate flows of the left, right, or both the left and right sides of the heart when called for.

In one embodiment, a catheter pump is disclosed. The catheter pump can include an elongated catheter body having a distal portion including an expandable cannula having an inlet and an outlet. The expandable cannula can have a delivery profile and an operational profile larger than the delivery profile. An impeller assembly can include an impeller shaft, and an impeller body can include one or more blades. The impeller blades can draw blood into the cannula when rotated. Further, an expandable support can have a mounting portion disposed on the impeller shaft distal of the impeller body and configured to maintain a position of the impeller relative to a cannula wall. In some embodiments, a motor can be disposed at a proximal end of the elongate catheter body, such that the motor remains remote from the impeller outside the patient in use. A re-sealable member can be disposed distally of the impeller in some embodiments. Further, the re-sealable member can be coupled with a bearing coupled with the impeller enabling the impeller to rotate in the bearing structure while holding the re-sealable member stationary distal of but aligned with the impeller.

In another embodiment, a catheter pump is disclosed. The catheter pump can comprise an elongated catheter body having a distal portion including an expandable cannula having an inlet and an outlet. The expandable cannula can have a delivery profile and an operational profile larger than the delivery profile. An impeller can include a tubular body and at least one blade disposed about the tubular body for drawing blood into the cannula when the impeller is rotated. A re-sealable member can be disposed distally of the tubular body in a guidewire passage. The re-sealable member can be coupled with the tubular body in a manner permitting the tubular body to rotate while the re-sealable member is not rotated.

In yet another embodiment, an apparatus for inducing motion of a fluid relative to the apparatus is disclosed. The apparatus can comprise a motor. An elongated catheter body can be coupled with the motor. The catheter body can include an expandable distal portion having an inlet and an outlet and a support structure disposed about a lumen. The expandable distal portion can have a delivery profile and an operational profile larger than the delivery profile. The apparatus can include an impeller comprising at least one impeller blade. The apparatus can further include an expandable impeller support having an arcuate outer surface in contact with the support structure at least when the expandable distal portion has the operational profile. Operation of the motor can cause rotation of the impeller to draw blood into the lumen. In some embodiments, the motor can be disposed at a proximal end of the elongate catheter body, such that the motor remains remote from the impeller outside the patient in use. A re-sealable member can be disposed distally of the impeller in some embodiments. Further, the re-sealable member can be coupled with a bearing coupled with the impeller enabling the impeller to rotate in the bearing structure while holding the re-sealable member stationary distal of but aligned with the impeller.

BRIEF DESCRIPTION OF THE DRAWINGS

A more complete appreciation of the subject matter of this application and the various advantages thereof can be realized by reference to the following detailed description, in which reference is made to the accompanying drawings in which:

FIGS. 6A and 6B show cross-sectional views of another embodiment of a distal bearing support.

Figure 1:
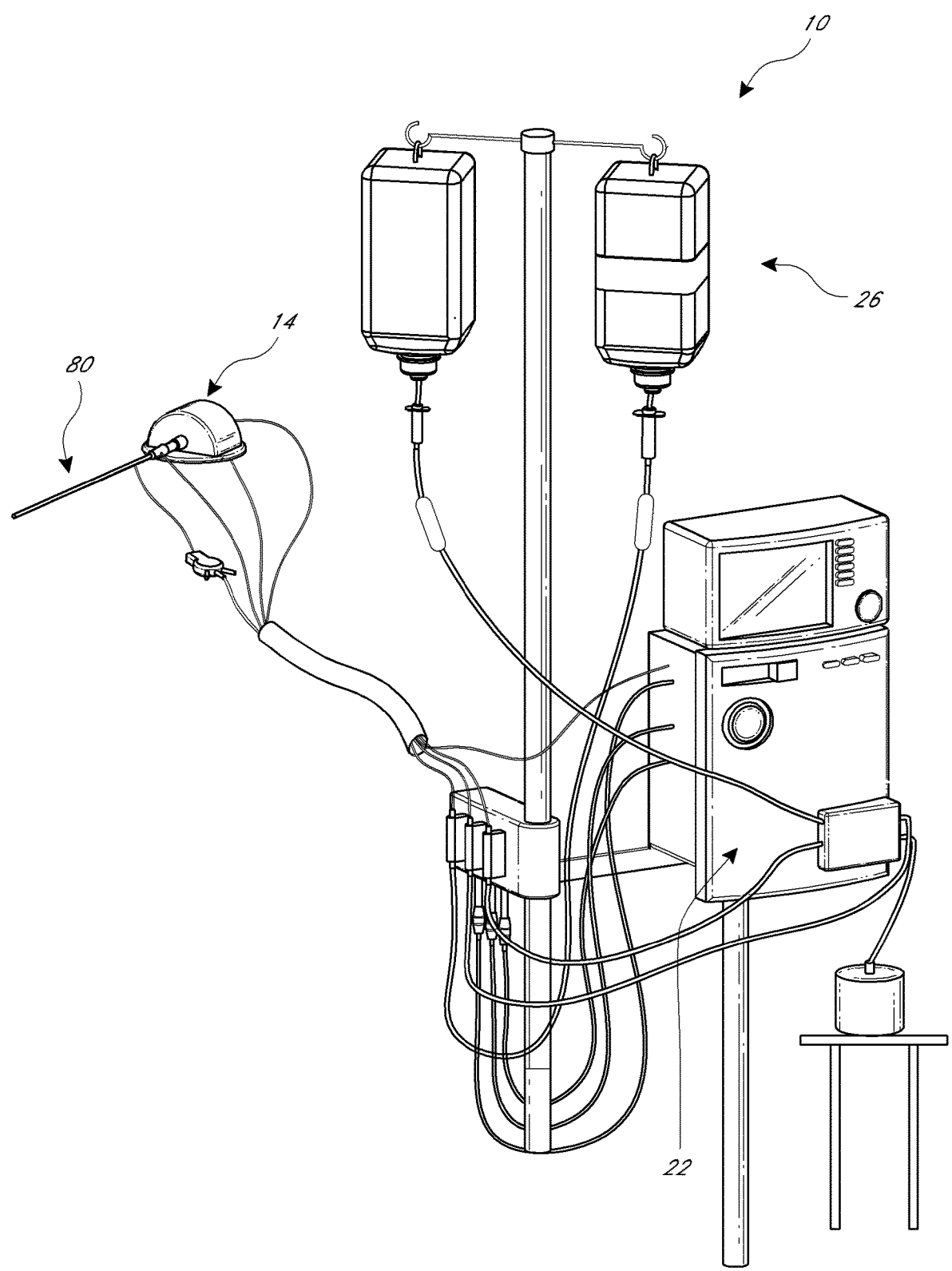
FIG. 1 illustrates one embodiment of a catheter pump configured for percutaneous application and operation.

More detailed descriptions of various embodiments of components for heart pumps useful to treat patients experiencing cardiac stress, including acute heart failure, are set forth below.

DETAILED DESCRIPTION OF THE PREFERRED EMBODIMENT

This application is directed to apparatuses for inducing motion of a fluid relative to the apparatus. In particular, the disclosed embodiments generally relate to various configurations for supporting an impeller disposed at a distal portion of a percutaneous catheter pump. As discussed in greater detail below, such supporting structure can be advantageous to minimize excursion of a high speed impeller toward or into a structure forming an inside surface of a cannula within which the impeller rotates. For example, in the disclosed embodiments, the cannula can be flexible, and the impeller can be flexibly supported off a distal end of the impeller shaft by a support member. In addition, the disclosed supporting structure can be advantageous at high impeller speeds and when the impeller and cannula are subject to hydraulic forces. The disclosed supports can act in various embodiments to maintain separation between the cannula and the impeller under various conditions. This support structure is particularly challenging for embodiments in which one or both of the impeller and cannula are collapsed or compressed for insertion of the pump. Furthermore, a re-sealable tip can be disposed near the distal end of the impeller. The re-sealable member can be configured to seal a guidewire guide tube when the guidewire guide tube and/or a guidewire are withdrawn from the pump.

I. Catheter Pump System and Method

FIGS. 1-4 show aspects of one embodiment of a catheter pump 10 that can provide high performance flow rates. Various additional aspects of the pump and associated components are similar to those disclosed in U.S. Pat. Nos. 7,393,181, 8,376,707, 7,841,976, 7,022,100, and 7,998,054 and U.S. Pub. Nos. 2011/0004046, 2012/0178986, 2012/0172655, 2012/0178985, and 2012/0004495, the entire contents of which are incorporated herein for all purposes by reference. In addition, this application incorporates by reference in its entirety and for all purposes the subject matter disclosed in each of the following concurrently filed applications: Application No. 61/780,656, entitled "FLUID HANDLING SYSTEM," filed on the same date as this application; application Ser. No. 13/801,833, entitled "SHEATH SYSTEM FOR CATHETER PUMP," filed on the same date as this application; application Ser. No. 13/802,570, entitled "IMPELLER FOR CATHETER PUMP," filed on the same date as this application; application Ser. No. 13/801,528, entitled "CATHETER PUMP," filed on the same date as this application; and application Ser. No. 13/802,468, entitled "MOTOR ASSEMBLY FOR CATHETER PUMP," filed on the same date as this application.

A. Catheter Pump System

The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes.

Figure 2:
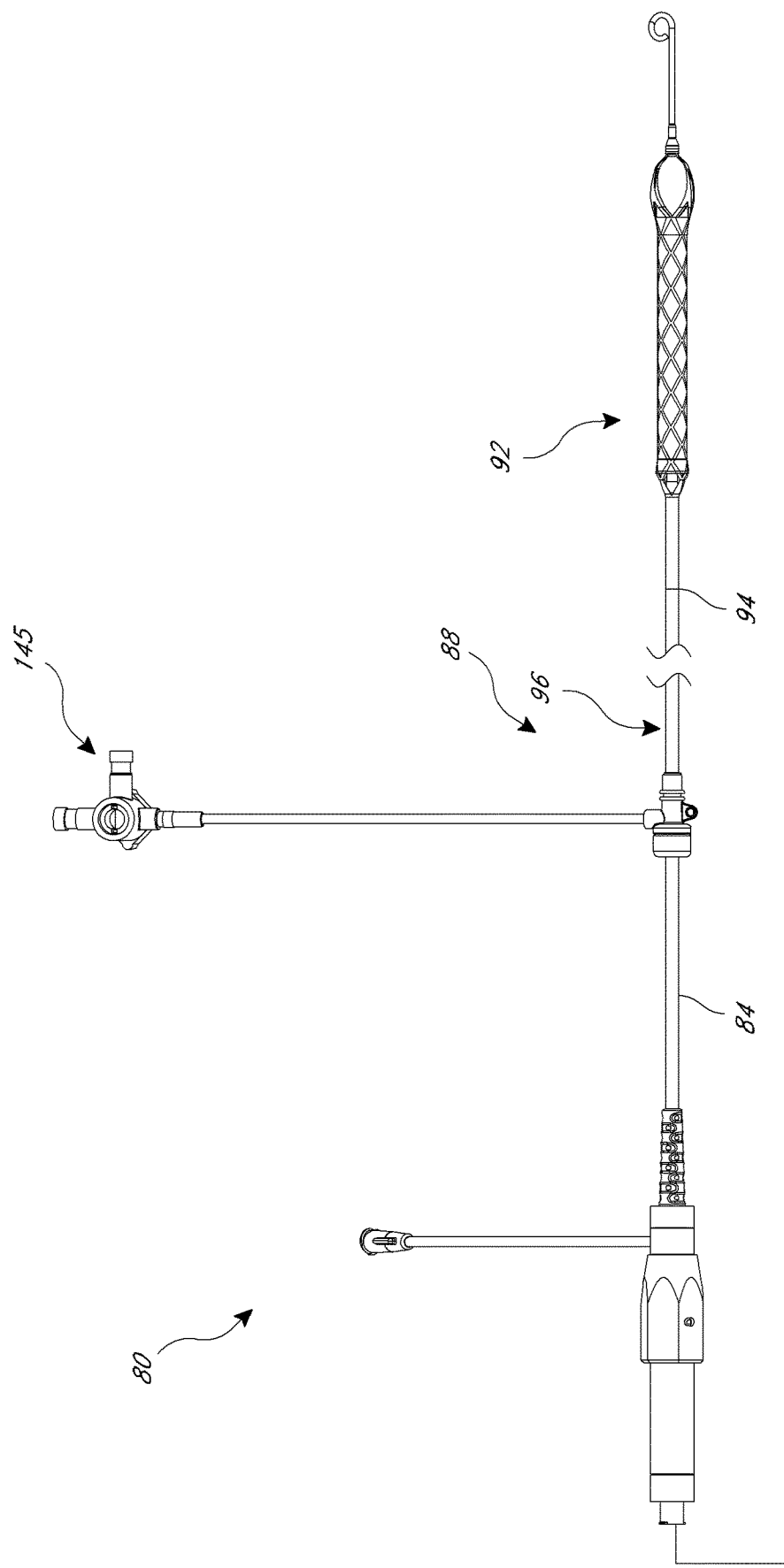
FIG. 2 is a plan view of one embodiment of a catheter assembly adapted to be used with the catheter pump of FIG. 1.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88.

One embodiment of a blood flow assembly 92 is coupled with the distal end of the catheter body 84. At least a portion of the blood flow assembly 92 is expandable and collapsible. For example, the blood flow assembly 92 can include an expandable and collapsible cannula. The cannula can be formed of a superelastic material, and in some embodiments, may have various shape memory material properties. The blood flow assembly 92 also can include an expandable and collapsible impeller. The cannula and impeller are discussed more below. In the collapsed state, the distal end of the catheter system 80 can be advanced to the heart, for example, through an artery. In the expanded state the blood flow assembly 92 is able to pump or output blood at high flow rates. FIGS. 2-4 illustrate the expanded state of one embodiment. The collapsed state can be provided by advancing a distal end 94 of an elongate body 96 of the sheath assembly 88 distally over the cannula of the blood flow assembly 92 to cause the blood flow assembly 92 to collapse. This provides an outer profile throughout the catheter assembly 80 that is of small diameter, for example a catheter size of about 12.5 Fr.

B. Impeller and Cannula Features, Deployment, and Operation

Figure 3A:
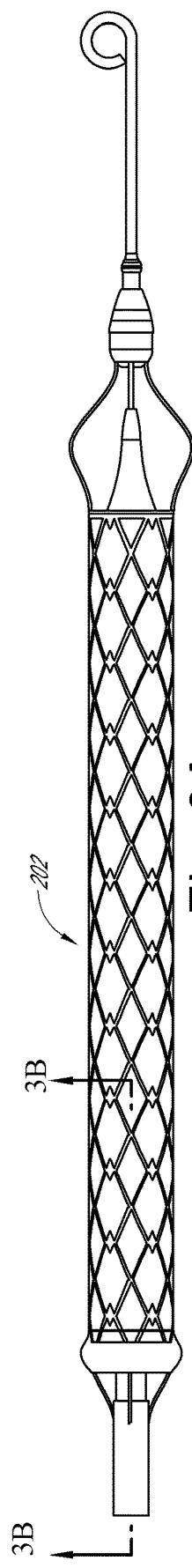
FIGS. 3A-3C illustrate the relative position of an impeller blade and an inner surface of an impeller housing in an undeflected configuration.
Figure 3B:
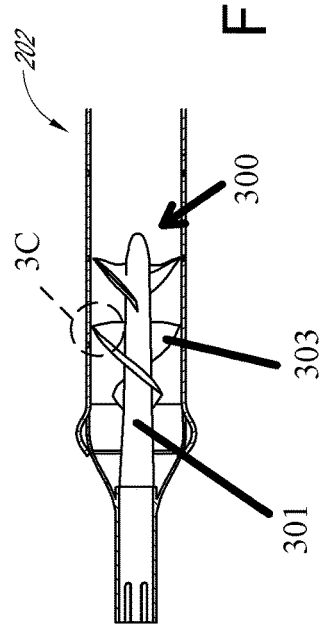
Figure 3C:
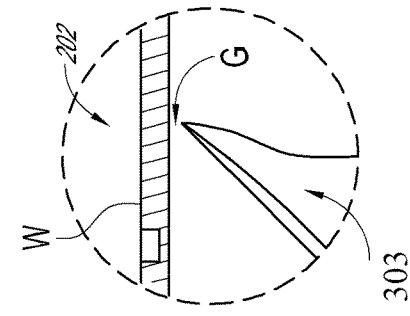
Figure 4:
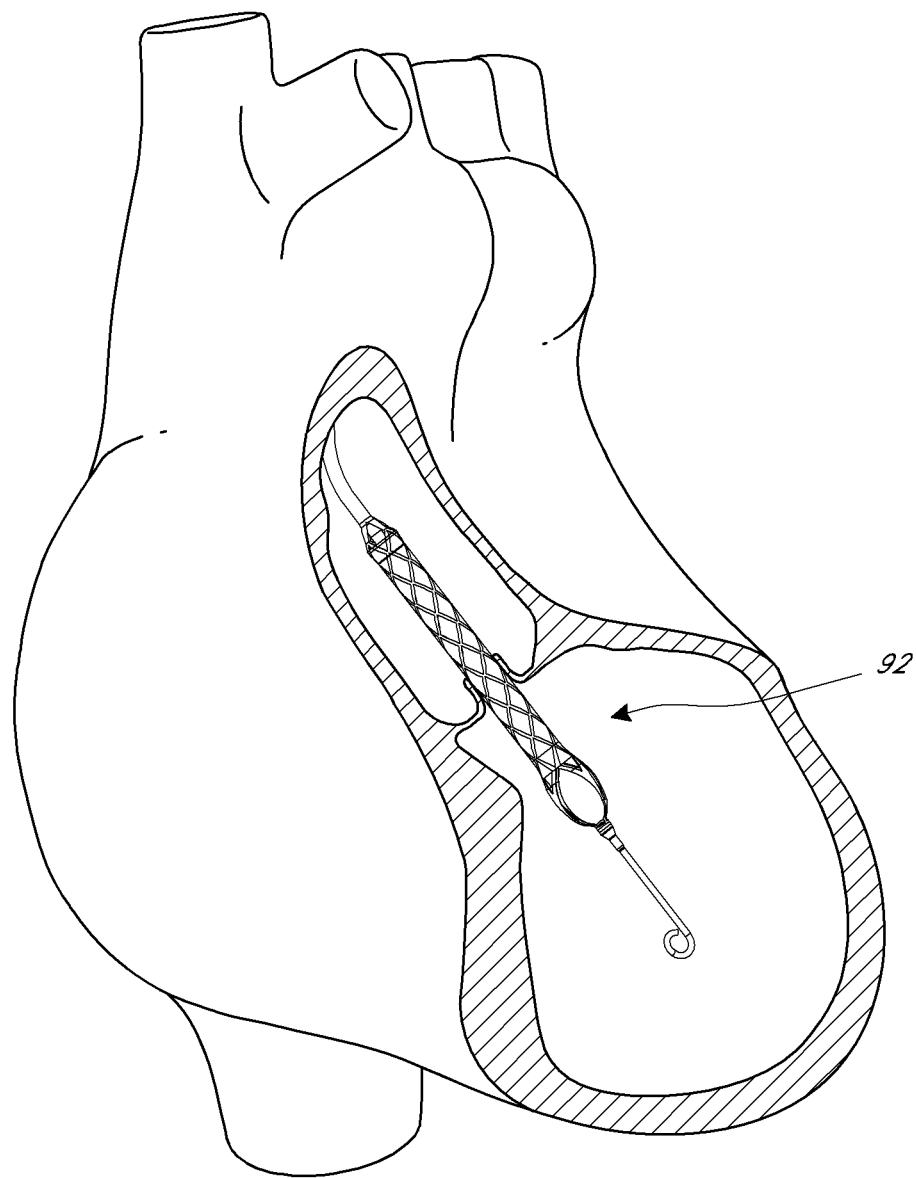
FIG. 4 shows the catheter assembly similar to that of FIG. 2 in position within the anatomy.

With reference to FIGS. 3A-3C, the operative device of the pump can include an impeller 300 having one or more blades 303. The one or more blades 303 can extend from an impeller hub 301. It can be desirable to increase the flow rate of the heart pump while ensuring that the impeller 300 can be effectively deployed within a subject. For example, an impeller can include one or more blades 303 that are configured to be inserted into a subject in a stored, or compressed, configuration. When the impeller 300 is positioned in the desired location, e.g., a chamber of a subject's heart as shown in FIG. 4, the blade(s) 303 of the impeller 300 can self-expand into a deployed or expanded configuration, in which the blade(s) 303 extends radially from a hub 301.

As shown in FIGS. 3A-3B, the impeller 300 can be positioned within a cannula or housing 202. A free end of the blades 303 can be separated from the wall W of the housing 202 by a tip gap G. The housing 202 can also have a stored, or compressed configuration, and a deployed or expanded configuration. The housing 202 and impeller 300 may deploy from the stored configurations from within the sheath assembly 88 into the expanded configuration. In such implementations, the sheath assembly 88 can keep the blade(s) 303 and the housing 202 compressed until the blade(s) 303 and housing 202 are urged from within a lumen of the sheath assembly 88. Once the blade(s) 303 are released from the sheath assembly, the blade(s) 303 can self-expand to a deployed configuration using strain energy stored in the blades 303 due to deformation of the blade(s) 303 within the sheath assembly 88. The expandable housing 202 may also self-deploy using stored strain energy after being urged from the sheath.

In the stored configuration, the impeller 300 and housing 202 have a diameter that is preferably small enough to be inserted percutaneously into a patient's vascular system. Thus, it can be advantageous to fold the impeller 300 and housing 202 into a small enough stored configuration such that the housing 202 and impeller 300 can fit within the patient's veins or arteries. In some embodiments, therefore, the impeller 300 can have a diameter in the stored configuration corresponding to a catheter size between about 8 Fr and about 21 Fr. In one implementation, the impeller 300 can have a diameter in the stored state corresponding to a catheter size of about 9 Fr. In other embodiments, the impeller 300 can have a diameter in the stored configuration between about 12 Fr and about 21 Fr. For example, in one embodiment, the impeller 300 can have a diameter in the stored configuration corresponding to a catheter size of about 12-12.5 Fr.

When the impeller 300 is positioned within a chamber of the heart, however, it can be advantageous to expand the impeller 300 to have a diameter as large as possible in the expanded or deployed configuration. In general, increased diameter of the impeller 300 can advantageously increase flow rate through the pump. In some implementations, the impeller 300 can have a diameter corresponding to a catheter size greater than about 12 Fr in the deployed configuration. In other embodiments, the impeller 300 can have a diameter corresponding to a catheter size greater than about 21 Fr in the deployed or expanded configuration.

In various embodiments, it can be important to increase the flow rate of the heart pump while ensuring that the operation of the pump does not harm the subject. For example, increased flow rate of the heart pump can advantageously yield better outcomes for a patient by improving the circulation of blood within the patient. Furthermore, the pump should avoid damaging the subject. For example, if the pump induces excessive shear stresses on the blood and fluid flowing through the pump (e.g., flowing through the cannula), then the impeller can cause damage to blood cells, e.g., hemolysis. If the impeller damages a large number of blood cells, then hemolysis can lead to negative outcomes for the subject. As will be explained below, various cannula and/or impeller parameters can affect the pump's flow rate as well as conditions within the subject's body.

When activated, the pump 10 can effectively increase the flow of blood out of the heart and through the patient's vascular system. In various embodiments disclosed herein, the pump 10 can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

C. Exemplary Left Ventricle Support Application

FIG. 4 illustrates one use of the catheter pump 10. A distal portion of the pump 10, which can include an impeller assembly 92, is placed in the left ventricle (LV) of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat.

Nos. 6,544,216; 7,070,555; and US 2012-0203056A1, all of which are hereby incorporated by reference herein in their entirety for all purposes.

II. Structures for Supporting a Distal Bearing

When the operative device, including at least the expandable cannula and the impeller, are positioned within the patient, the operative device can be subject to bending loads. If the operative device is disposed in a heart chamber, the bending loads can be caused by movement of the beating heart or other external loads. The gap G between the blade(s) of the impeller and the internal wall of the expandable cannula can be very small, on the order of ten-thousandths of an inch. Due to the small gap between the cannula and the impeller blades, the bending loads can cause the impeller to contact the inner wall of the expandable cannula. When the impeller contacts the cannula while it rotates at high speed, the impeller and/or the cannula can be damaged. In addition, blood cell damage can result from contact between the impeller impacting the wall of the expandable cannula if, for example, the cells are caught between these components. Because the impeller rotates at high speed, an undesirable closing of the gap between the blade and cannula inner diameter for even a short time can lead to damage of a significant number of blood cells. Preventing damage to a large number of blood cells is advantageous, making the system less invasive by minimizing negative side effects of the use of the catheter pump system. Thus, while the small "tip gap" can advantageously improve the performance of the pump, the pump systems disclosed herein are advantageously configured to minimize the risk of adverse events (e.g. hemolysis and bleeding), which is generally undesirable in heart pump systems.

A. Exemplary Distal Bearing Support Having Improved Bending Stiffness

One approach to controlling tip gap is to improve the bending stiffness of the operative device. For example, the impeller and/or cannula housing can be configured to reduce movement of the impeller blade(s) relative to the inner wall of the cannula housing. In particular, increased stiffness of the operative device can reduce deflection of the impeller toward the cannula housing and/or deflection of the cannula housing toward the impeller. In one approach, the pump system is configured so that the impeller does not move significantly relative to the cannula housing, even though both can move together within the ventricle. In various embodiments, a distal bearing support can be disposed near, e.g., mounted, adjacent to a distal portion of the impeller shaft.

Figure 5A:
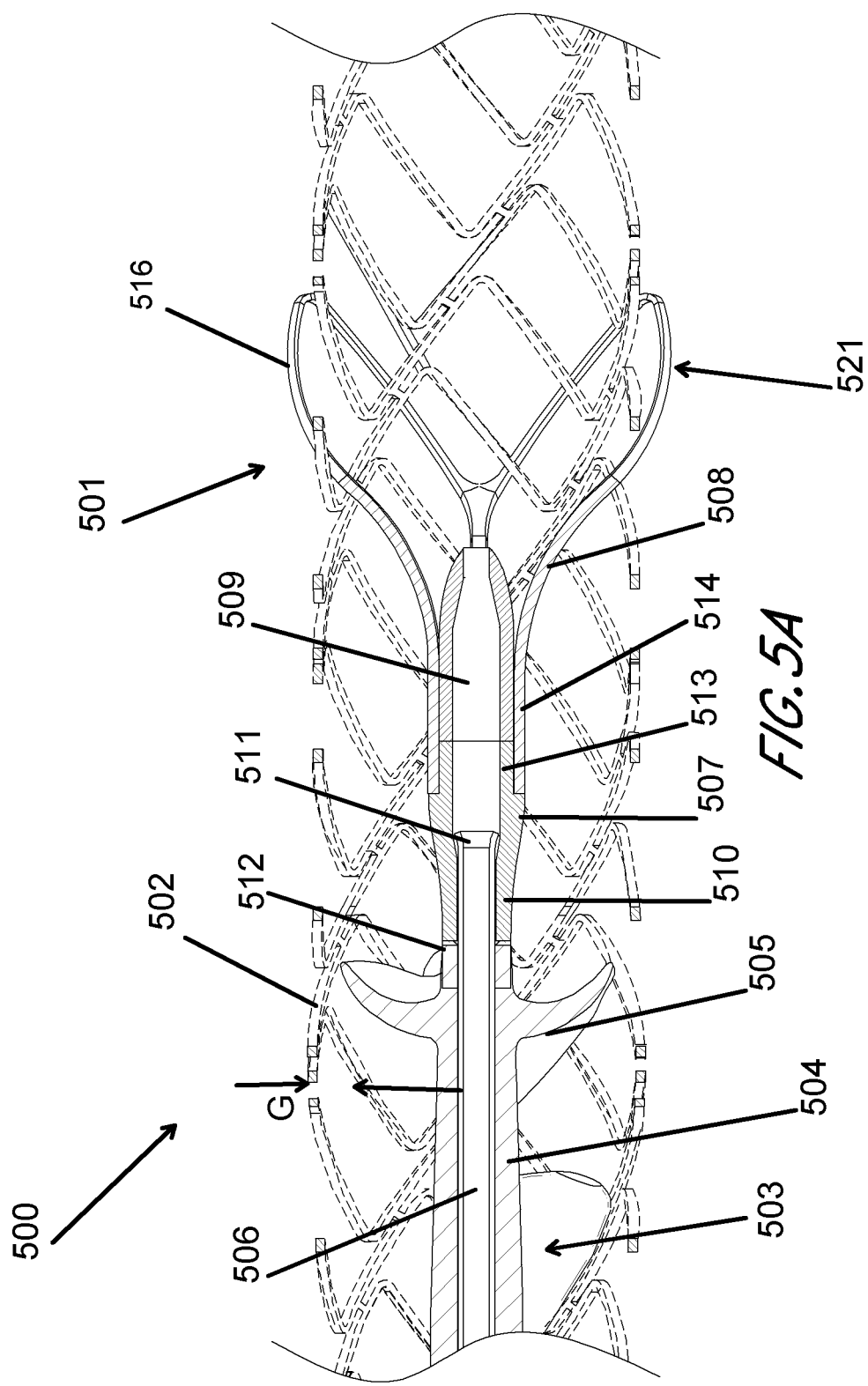
FIGS. 5A-5B show cross-sectional views of one embodiment of a distal bearing support.
Figure 5B:
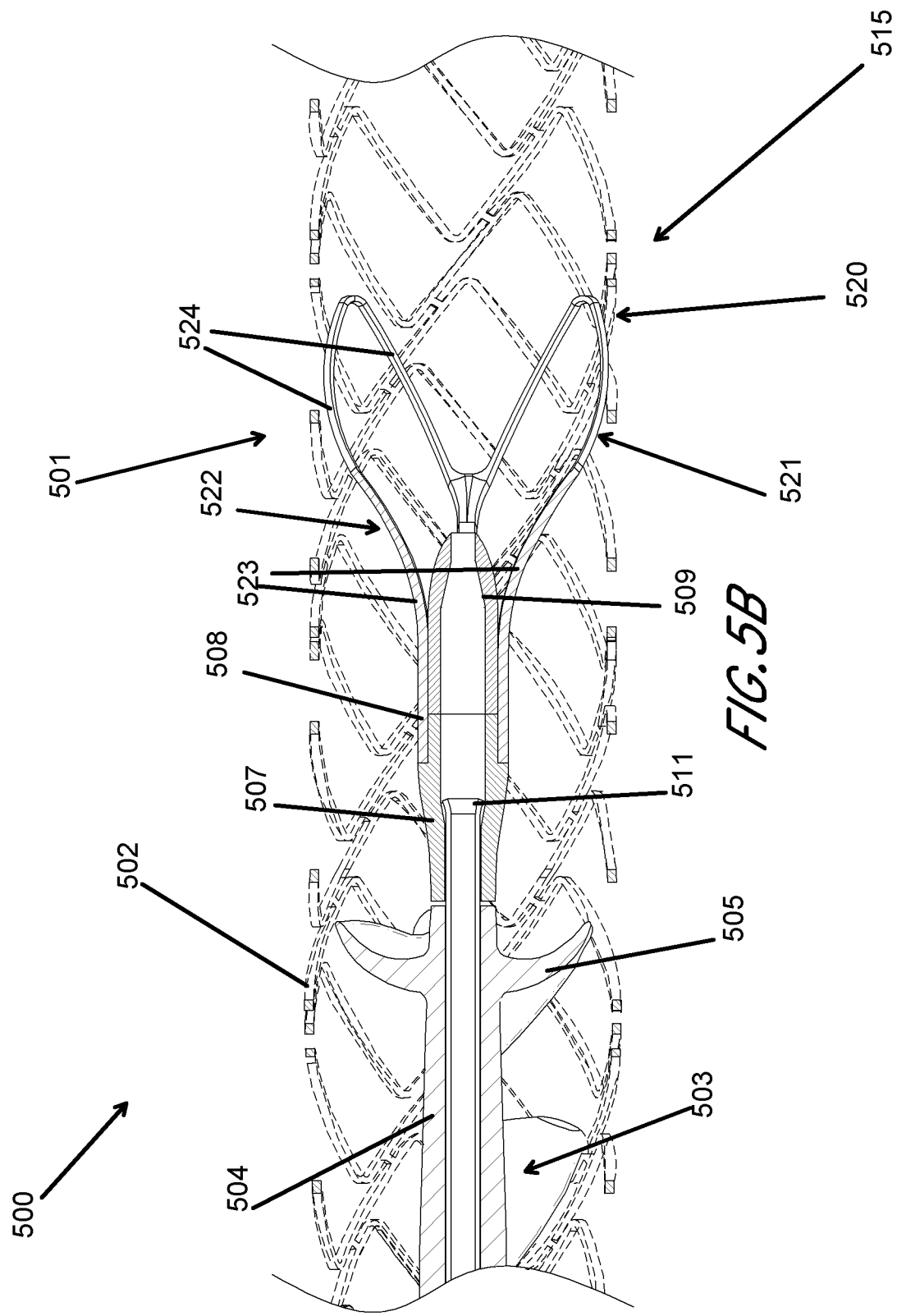

FIG. 5A is a side cross-sectional view of an operative device 500 of a catheter pump, according to one embodiment, having a support member in an expanded or relaxed configuration. FIG. 5B is a side cross-sectional view of the operative device 500 of FIG. 5A, with the support member illustrated as deployed within a cannula. For example, the operative device 500 can include a cannula housing 502, an impeller 503 disposed within the cannula housing 502, and one example of a distal bearing support 501 configured to improve the bending stiffness of the operative device 500. In FIG. 5A, the cannula housing 502 in an expanded configuration is shown in outline to compare a diameter of the expanded cannula housing 502 with a diameter of the distal bearing support 501 in a relaxed state. Thus, it should be appreciated that the configuration of FIG. 5A (e.g., showing the distal bearing support 501 as extending through the walls of the cannula housing 502) is for illustration purposes only.

The impeller 503 can include an impeller hub 504 and one or more blades 505 extending from the hub 504. The hub 504 can be mounted to an impeller shaft 506 such that the hub 504 is rotatably fixed relative to the impeller shaft 506, e.g., the hub 504 rotates with the shaft 506. As explained herein, the space between the free end of the blade(s) 505 and an inner wall of the cannula housing 502 can define a tip gap G. When the operative device 500 is subjected to bending loads, the free end of the blade(s) 505 may contact the inner wall of the cannula housing 502. As explained above, blood flowing between the free end of the blade(s) 505 and the cannula housing 502 may be damaged when the blade(s) 505 impacts the cannula housing 505, which can negatively affect patient outcomes.

As shown in FIG. 5A, the distal bearing support 501 can comprise a mounting portion 507 coupled to a distal portion of the impeller shaft 506, a support member 508 coupled to the mounting portion 507, and a nose member 509 (also referred to as a cap in some arrangements) disposed distal of the mounting portion 507. The nose member 509 can be disposed within and can be coupled to the support member 508. Preferably, the mounting portion 507, nose member 509, and support member 508 are configured to be non-rotatably mounted to the impeller shaft 506. For example, at least a proximal portion 510 of the mounting portion 507 disposed over a distal portion 511 of the impeller shaft 506 can have an inner diameter that is greater than an outer diameter of the impeller shaft. The impeller shaft 506 can therefore rotate relative to the mounting portion 507, such that the mounting portion 507 does not rotate with the impeller shaft 506. The interface between the mounting portion 507 and the impeller shaft 506 is preferably relatively low friction to minimize heat generation and a torque resistance applied to the distal end 511 of the impeller shaft 506.

During assembly of the distal bearing support 501, the mounting portion 507 can slide over the distal end 511 of the impeller shaft 506. As discussed above, the mounting portion 507 may be journaled in, e.g., not rotationally fixed relative to, the impeller shaft 506 in the illustrated embodiment. In some embodiments, a tool can be inserted into the distal end 511 of the impeller shaft 506 to flare the distal end 511 to make it wider than the proximal portion 510 of the mounting portion 507, e.g., the portions of the mounting portion 507 situated around the impeller shaft 506 proximal to the flared distal end 511. The flared distal end 511 can thereby prevent mounting portion 507 from translating distally and disengaging from the impeller shaft 506. In some embodiments, the mounting portion 507 can be made of a polymer, such as PEEK. Because the mounting portion 507 is not fixed relative to the impeller shaft 506, the impeller shaft 506 is free to rotate within the mounting portion 507. Moreover, in some aspects, an optional ring member 512 can be positioned around the impeller shaft 506 between the mounting portion 507 and the impeller 503. The ring member 512 can act as an interface between the impeller 503 and the mounting portion 507, and in some implementations, can be formed of a Teflon® (PTFE) or other low friction material.

As shown in FIGS. 5A-5B, the support member 508 can be disposed over a distal portion 513 of the mounting portion 507. The distal portion 513 of the mounting portion 507 can include a necked or stepped region to engage the support member 508. A mechanical connection may be provided between the support member 508 and another rotationally fixed portion of the distal bearing support 501, e.g., between a proximal portion of the support member 508 and the mounting portion 507. For example, the mounting portion 507 can include one or more barbs (not shown) positioned around the circumference of the mounting portion 507. In some implementations, the barbs are located every 120 degrees about the circumference. The barbs can engage corresponding slots in the support member 508 to secure the support member 508 to the mounting portion 507. The barbs could alternatively be formed on the support member 508 and configured to extend into and engage the mounting portion 507 in one embodiment. In some arrangements, an adhesive connection is provided between the mounting portion 507 and support member 508 in place of or in addition to the mechanical connection. In another embodiment, the support member 508 and mounting portion 507 are portions of a unitary body, which can be formed from a cylindrical precursor tube. In some embodiments, the support member can be formed of nitinol.

The nose member 509 can be positioned distal of the mounting portion 507 and within the proximal portion 514 of the support member 508. Like the mounting portion 507, the nose member 509 can additionally or alternatively include barbs (not shown) around the circumference of the nose member 509 (e.g., separated by 120 degrees) to engage corresponding slots in the support member 508. The nose member 509 can be configured to smooth out the flow of blood through the cannula housing 502 in the zone of the distal bearing support 501, e.g., distal of the impeller 503.

Thus, the mounting portion 507 can be mounted about the impeller shaft 506 (restrained axially by the flared portion 511 but otherwise rotationally decoupled from the impeller shaft 506), the support member 508 can couple to the mounting portion 507 via the barbs, and the nose member 509 can couple to the support member 508 via additional barbs. In some embodiments a single continuous member is provided that combines the function of the nose portion 509 and mounting portion 507. For example, these components can be formed as a unitary component to which the support member may be coupled.

The support member 508 can include a stiffener structure, e.g., a skeleton, cage-like, or other flexible structure that extends distally from or of the nose member 509 and/or mounting portion 507. For example, the support member 508 may include one or more lobes 516 or digits biased to expand radially outward. As shown in FIG. 5A, the support member 508 can be sized and shaped such that the radial distance from one or more of the lobes 516 or digits to a projection of the longitudinal axis of the impeller shaft 506 in their natural, relaxed state is greater than the radial distance from the cannula wall to a projection of the longitudinal axis of the impeller shaft 506 when the cannula 502 is in an operational (e.g., expanded) configuration. When the lobes 516 or digits are positioned within the cannula 502 with the cannula 502 in an expanded state (e.g., as in FIG. 5B), the digits or lobes 516 can apply a radially outward force against the inner wall of the cannula housing 502. This radially outward force can increase the bending stiffness of the cannula housing 502. By increasing the bending stiffness of the cannula housing 502, the disclosed distal bearing support 501 can reduce the risk of hemolysis during operation of the pump.

As shown in FIGS. 5A-5B, the lobes 516 may comprise an elongate member, e.g., an elongate arcuate member or compound curve, extending from the proximal portion 514 of the support member 508. The lobes 516 can include a concave portion 522 disposed between the proximal portion 514 of the support member 508 and a free end of the lobes, e.g., near the proximal portion 514 in some arrangements.

The concave portion 522 can be curved inwardly towards the interior of the cannula 502. Furthermore, the lobes 516 can have a convex portion 521 in contact with a support region 520 of the cannula housing 502. The convex portion 521 can be curved outwardly towards the wall of the cannula 502 in some embodiments. It should be appreciated that, due to the radially outward bias of the lobes 516, the convex portion 521 of the lobes 516 may induce a radially outward force against the cannula housing 502 at the support region 520, where the convex portion 521 contacts the cannula housing 502.

Various embodiments of the cannula housing 502 may comprise a mesh of metallic material that is coated by an elastic film. In some cases, the radially outward force applied by the convex portions 521 against the cannula housing 502 may deform or otherwise damage the metallic mesh and/or the elastic covering film. To prevent deformation of the cannula housing 502 and/or damage to the elastic film, in some embodiments, the metallic mesh may be made denser at the support region 520 of the cannula wall that contacts the convex portions 521 than in other locations of the cannula housing 502. The additional metallic material at the support region 520 near the convex portions 521 can provide additional support for the housing 502 and elastic film to prevent undesirable deformation of the housing 502 and/or film.

In the illustrated embodiment, the support member 508 deploys into a flower-shape, e.g., the lobes 516 may form the shape of flower petals, and/or non-planar, compound curve or isomorphic shape. The exemplary embodiment has four lobes 516. Each lobe 516 may be formed or defined by a pair of proximal struts 523 and a pair of distal struts 524. As shown in FIG. 5B, for example, each proximal strut 523 may be coupled or formed with the proximal portion 514 of the support member 508. The proximal struts 523 may be spaced apart circumferentially about the mounting portion 507 and/or the nose member 509. Distal ends of the proximal struts 523 may couple to proximal ends of the distal struts 524, as shown in FIGS. 5A-5B. Distal ends of the distal struts 524 may couple to one another. As shown in FIG. 5B, for example, the convex portion 521 of the lobes 516 may be disposed between the proximal and distal ends of the distal struts 524.

As shown in FIG. 5B, a distal end 515 of each of the exemplary lobes 516 may extend generally parallel with the cannula housing and curves slightly inward at its tip toward the impeller axis to avoid the edges from cutting into the cannula housing 502. Further, the outer curved faces of the lobes 516 or digits may not be rigidly fixed to the inner surface of the cannula housing 502 but, instead, relative movement between the two may be possible. This relative movement enables easier expansion and collapsing of the operative device of the catheter pump system. One will appreciate from the description herein that the support member 508 stored and deployed configurations can be modified depending on the application, and in various examples, based on the impeller and cannula housing designs.

B. Exemplary Distal Bearing Support with Enhanced Maneuverability

While the distal bearing support of FIGS. 5A-5B can advantageously stiffen the operative device of the catheter pump system, the support member extends distally beyond the distal end of the impeller shaft (and/or the impeller). Because the stiff support member extends beyond the distal end of the impeller and/or impeller shaft (e.g., axially displaced from the distal end of the impeller shaft), a length of the catheter pump extending from a proximal portion of the impeller to the distal end of the support member can have a relatively high bending stiffness, because this portion includes the relatively stiff impeller in addition to the support member. This length can be referred to as the "stiff length." A long stiff length can be disadvantageous because it can hamper maneuverability when the catheter pump (the operative device) is urged through the arcuate-shaped aortic arch. Thus, it can be desirable to decrease the length of the "stiff length" portion of the catheter pump while still maintaining a high bending stiffness when the operative device is positioned in or near a heart chamber, e.g., the left ventricle.

Figure 6A:
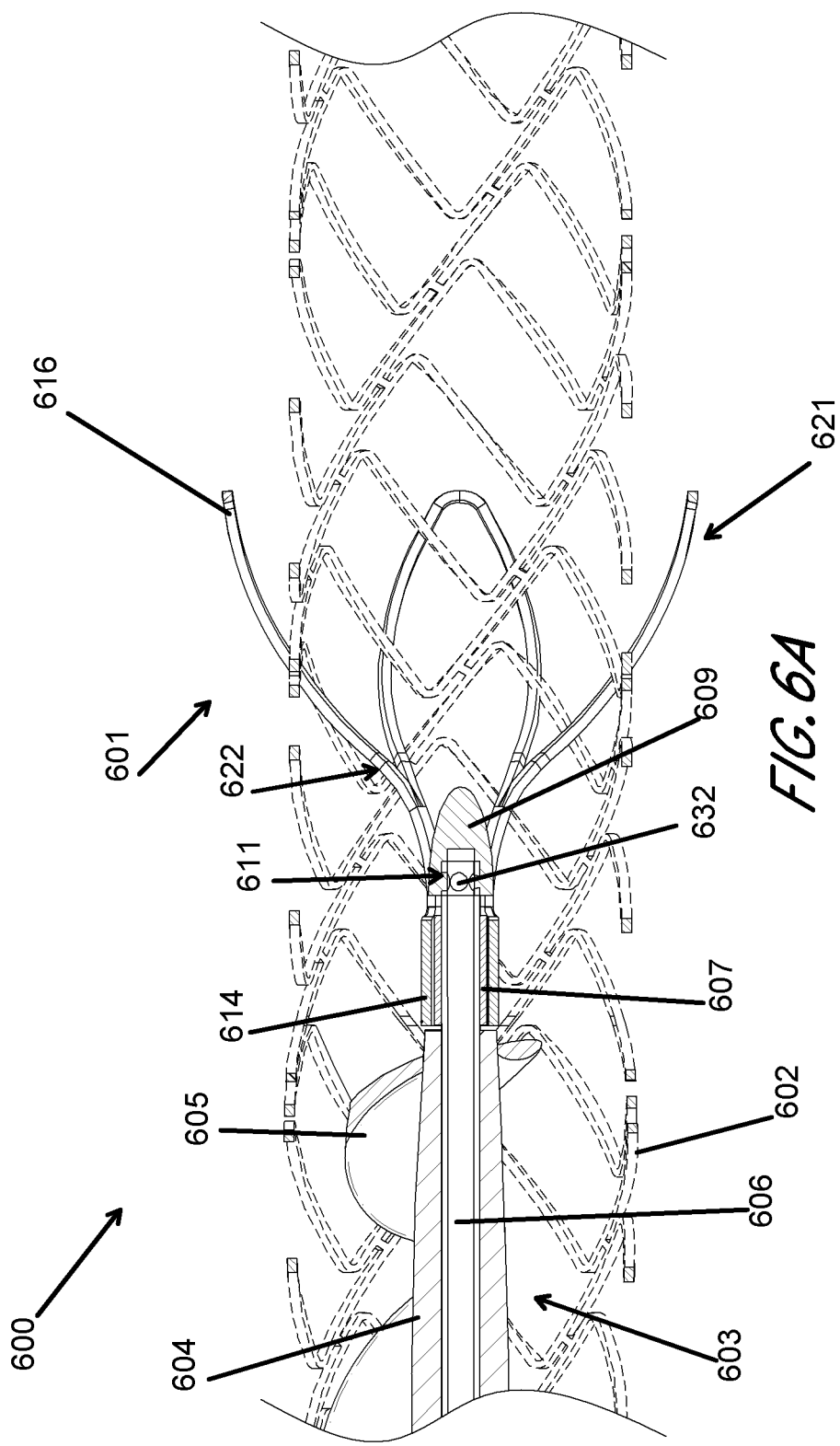

1. Exemplary Distal Bearing Support for Enhanced Maneuverability of the Operative Device FIG. 6A is a side cross-sectional view of an operative device 600 of a catheter pump, according to another embodiment, with a support member in an expanded or relaxed configuration. FIG. 6B is a side cross-sectional view of the operative device 600 of FIG. 6A, with the support member illustrated as being disposed in a cannula. Unless otherwise noted, the reference numerals of FIGS. 6A-6B may refer to components similar to those referenced above in FIGS. 5A-5B, incremented by 100 relative to FIGS. 5A-5B. For example, the operative device 600 can include a cannula housing 602, an impeller 603 disposed within the cannula housing 602, and another example of a distal bearing support 601 configured to improve the bending stiffness and maneuverability of the operative device 600. The impeller 603 can include an impeller hub 604 mounted on an impeller shaft 606 and one or more blades 605 extending from the hub 604. As with FIG. 5A above, FIG. 6A illustrates the distal bearing support 601 in a relaxed state for illustration purposes only.

As in FIGS. 5A-5B, the distal bearing support 601 can include a nose member 609 or cap configured to smooth the flow of blood. In addition, the distal bearing support 601 can include a support member 608 having a plurality of lobes 616 extending radially outward with a radially outward bias when positioned in the cannula housing 602. As in FIGS. 5A-5B, the lobes 616 can include a concave portion 622 and a convex portion 621 that contacts the mesh of the cannula housing 602 at a support region 620. Further, the lobes 616 can include an arcuate member with a pair of separate proximal struts 623, and a pair of distal struts 624 coupling at their distal ends.

However, unlike the distal bearing support 501 in FIGS. 5A-5B, the distal bearing support 601 of FIGS. 6A-6B can provide a reduced stiff length, while increasing the bending stiffness when the pump is positioned within a heart chamber. As illustrated in FIGS. 6A-6B, at least a proximal portion 614 of the support member 608 axially overlaps with the impeller shaft 606, as opposed to being axially displaced from the distal end 511 of the impeller shaft 506, as in the embodiment of FIG. 5A. Stated another way, an axial gap or spacing is provided between the distal-most aspect of the impeller shaft 506 (e.g., the distal end 511) and the proximal-most aspect of the support member 508 in the embodiment of FIG. 5A, whereas no axial gap is provided between the distal-most aspect 611 of the impeller shaft 606 and the proximal-most aspect of the support member 608 in the embodiment of FIG. 6A. The length of the stiff portions (e.g. the "stiff length") can thereby be reduced as compared with the embodiment of FIGS. 5A-5B. Indeed, because the support member 608 of FIGS. 6A-6B extends distally beyond the distal end 611 of the impeller shaft 606 by a lesser amount than the support member 508 of FIGS. 5A-5B, the stiffness of the operative device 600 may be less in the embodiment of FIGS. 6A-6B. The operative device 600 of FIG. 6 may therefore be easily maneuvered over the aortic arch during insertion.

For example, in FIG. 6A, a mounting portion 607 (e.g., an interface material) can be positioned over, e.g., formed around, the impeller shaft 606 to rigidly couple to the shaft 606. In some embodiments, the mounting portion 607 can comprise a PEEK heat shrink material that can be applied over the impeller shaft 606 and can rotate with the shaft 606. For instance, the heat shrink material can be applied before forming the impeller 603, e.g., by casting. The nose member 609 can be molded to the impeller shaft 606. In some embodiments, the distal end 611 of the impeller shaft 606 can include engagement features 632 for enhancing security of the nose member 609 to the shaft 606. The engagement features 632 can include circumferential recesses or holes, e.g., formed by laser drilling. When the nose member 609 is molded over the distal end 611, portions of the nose member 609 can reflow into the circumferential holes to help secure the nose member 609 to the distal end 611 of the impeller shaft 606.

The proximal portion 614 of the support member 608 can be mounted over the mounting portion 607 to secure the support member 608 to the impeller 603. In some embodiments, a nitinol support member 608 can be cooled to expand the proximal end 614 of the support member 608 to allow the proximal end 614 to be urged over the mounting portion 607. When the support member 608 returns to room temperature, the nitinol can return to its original size. The proximal end 614 of the support member 608 can include one or more slots circumferentially spaced from one another on the proximal end 614 of the support member 608. Each of the one or more slots can extend from the proximal-most side of the support member 608 distally and terminate at a wider hole region. The slots can be formed through the thickness of the proximal end portion 614 of the support member 608. In some embodiments, the slots extend through the entire thickness of the proximal end portion 614 of the support member 608, but in other embodiments, the slots may only extend partially through the thickness. The slots can be used to expand or flare out the proximal end 614 of the support member 608 when the support member 608 is urged over the nose member 609 to couple to the mounting portion 607. This expansion or flaring can advantageously assist in mounting the support member 608 over the nose member 609. The mounting portion 607 (spinning with the impeller shaft 606) can freely rotate within the proximal end 614 of the support member 608. As above, the support member 608 can provide enhanced bending stiffness. In addition, as explained herein, the support member 608 can provide improved maneuverability of the operative device 600 by reducing the stiff length of the operative device 600.

2. Exemplary Maneuverable Distal Support with Sealable Guide Wire Lumen

Although the distal bearing support 601 illustrated in FIGS. 6A-6B can provide improved bending stiffness and a reduced stiff length, there may be a few potential problems with the embodiment of FIGS. 6A-6B. For example, the molded nose member 609 of FIGS. 6A-6B may be susceptible to damage during operation of the pump, and the nose member 609 may break off the impeller shaft 606 under various operational or environmental conditions. Moreover, in the embodiment of FIGS. 6A-6B, the support member 608 can translate axially in the distal direction, which may cause the support member 608 to jam against the nose member 609 when the support member 608 translates distally. If the support member 608 bears against the nose member 609, the nose member 609 could break, or the resulting distally-directed force could slow or stop rotation of the impeller shaft 606.

Furthermore, when a Seldinger insertion technique is used to advance the operative device to the heart, a guidewire and guidewire guide tube may be used. For example, the guidewire guide tube may be disposed through a central lumen of the catheter pump. The clinician can insert a guidewire through the guidewire guide tube, and can advance the guidewire to the heart. After advancing the operative device over the guidewire and into the heart, the guidewire and guidewire guide can be removed from the catheter pump. When the guidewire guide tube and/or the guidewire is retracted through a distal portion of the nose member 609, the distal portion may not adequately reseal the lumen through the impeller shaft. Accordingly, there is a need for an improved distal bearing support that provides for a re-sealable nose member and an improved support member.

Figure 7A:
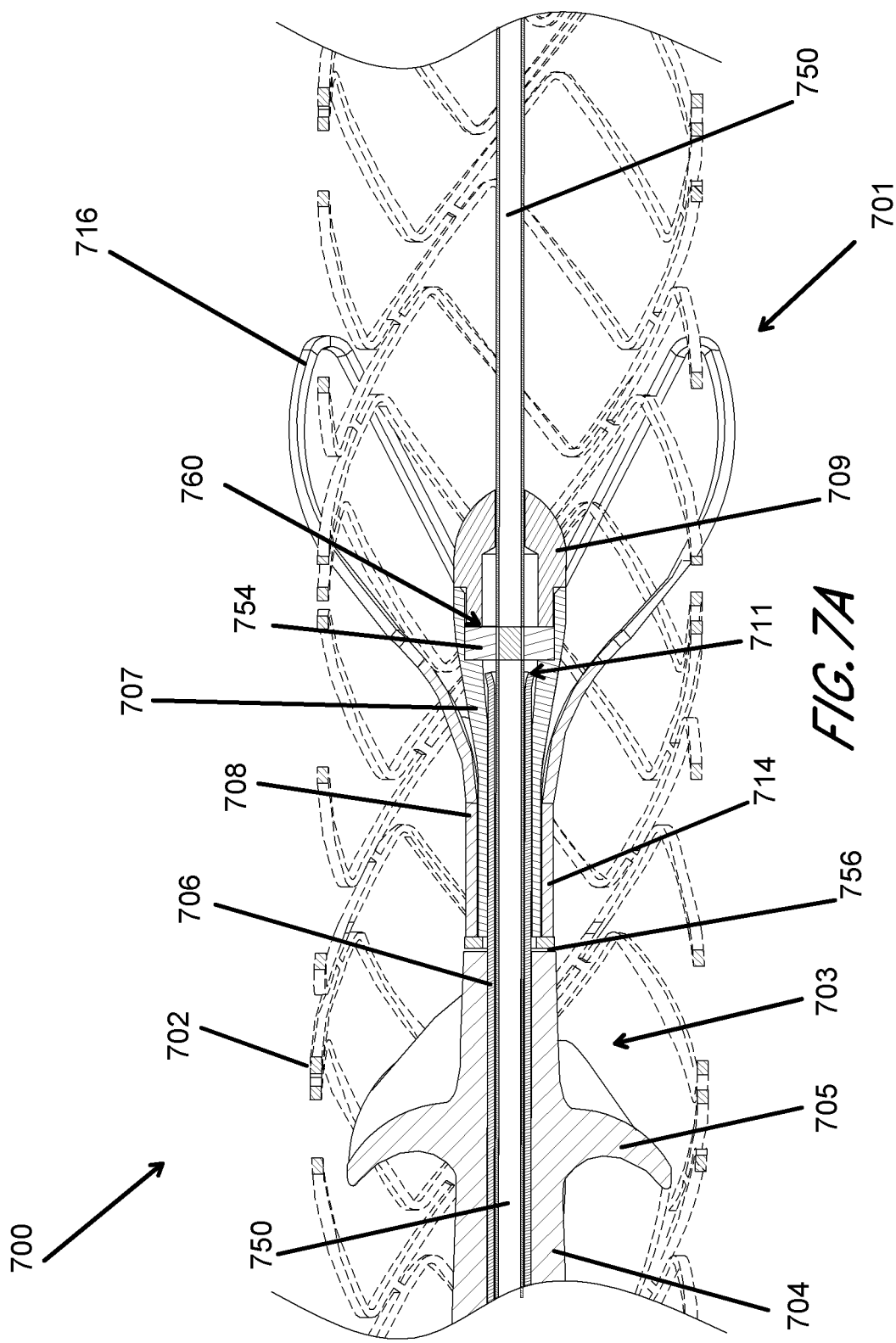
FIGS. 7A and 7B show cross-sectional views of yet another embodiment of a distal bearing support, and also illustrate a guide wire guide device.
Figure 7B:
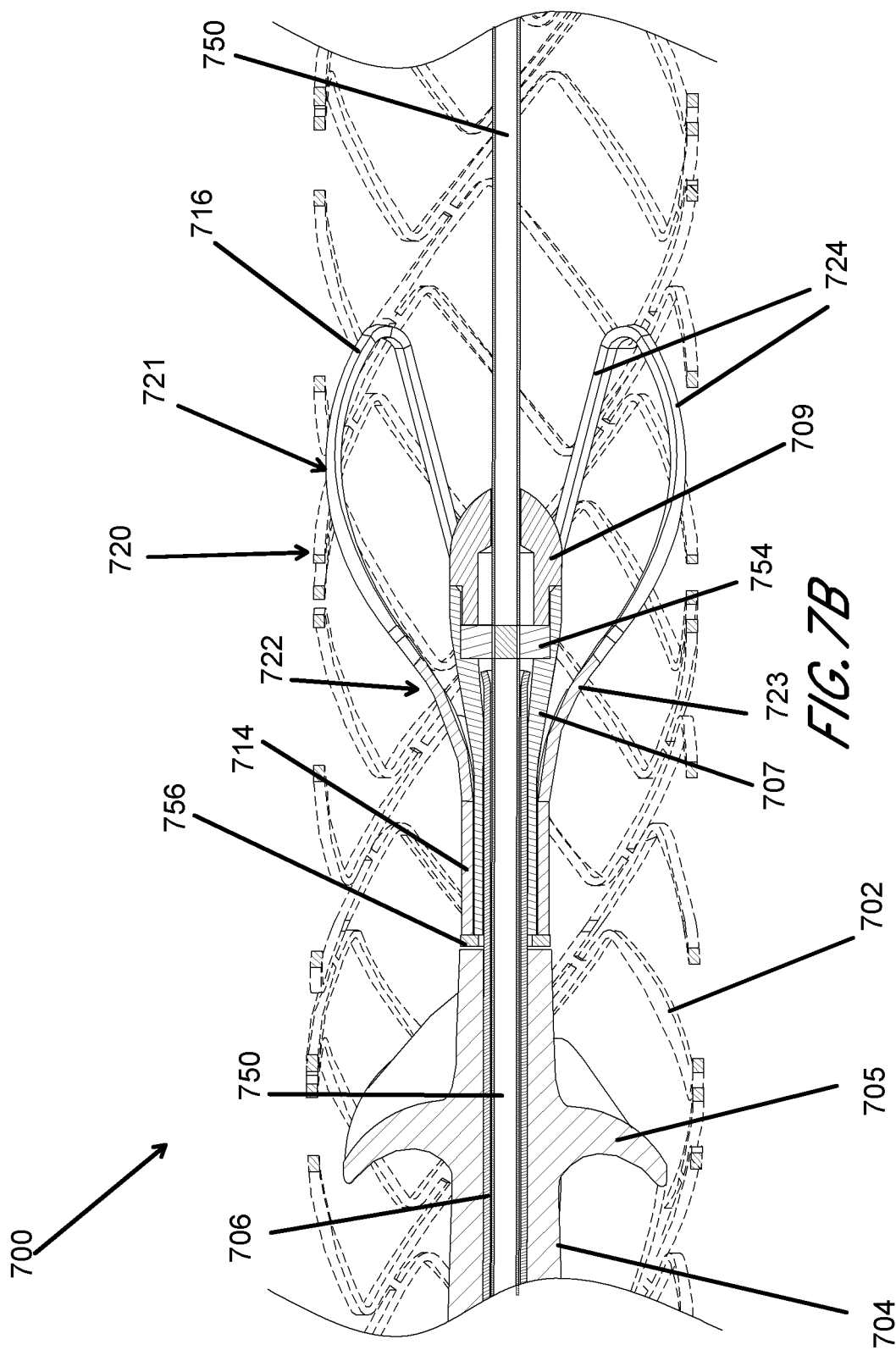

FIG. 7A is a side cross-sectional view of an operative device 700 of a catheter pump, according to another embodiment, with a support member in an expanded or relaxed state or configuration. FIG. 7B is a side cross-sectional view of the operative device 700 of FIG. 7A, with the support member shown as being disposed in the cannula. Unless otherwise noted, the reference numerals of FIGS. 7A-7B may refer to components similar to those referenced above in FIGS. 5A-5B and 6A-6B, incremented by 100 relative to FIGS. 6A-6B. For example, the operative device 700 can include a cannula housing 702, an impeller 703 disposed within the cannula housing 702, and another example of a distal bearing support 701 configured to improve the bending stiffness and maneuverability of the operative device 700. The impeller 703 can include an impeller hub 704 mounted on an impeller shaft 706 and one or more blades 705 extending from the hub 704. As with FIG. 5A above, FIG. 7A illustrates the distal bearing support 701 in a relaxed state for illustration purposes only.

In addition, as in FIGS. 5A-5B and 6A-6B, the distal bearing support 701 can include a nose member 709 or cap configured to smooth the flow of blood. The distal bearing support 701 can also include a mounting portion 707 configured to mount to the impeller shaft 706, and a support member 708 coupled to the mounting portion. The support member 708 can have a plurality of lobes 716 extending radially outward with a radially outward bias when positioned in the cannula housing 702. The lobes 716 can include a concave portion 722 and a convex portion 721 that contacts the mesh of the cannula housing 702 at a support region 720. Further, the lobes 716 can include an arcuate member with a pair of separate proximal struts 723, and a pair of distal struts 724 coupling at their distal ends. In addition, a guidewire guide tube 750 can pass through the impeller shaft 706. As explained above, a guidewire can be advanced through the guidewire guide tube and into the patient's anatomy. As with FIGS. 6A-6B, a proximal portion 714 of the support member 708 overlaps a distal end 711 of the impeller shaft, which can reduce the stiff length of the operative device 700.

The support member 708 can initially be mounted loosely over the distal portion 711 of the impeller shaft 706. A spacer or washer 756 (e.g., formed of nitinol) can be formed at or near the proximal end portion 714 of the support member 708 to prevent distal motion of the support member 708 in the axial direction. For example, the washer 756 can be welded to the proximal end 714 of the support member 708 in some embodiments. The mounting portion 707 can be glued or otherwise secured to the impeller shaft 706 within the support member 708 such that the mounting portion 707 rotates with the shaft 706 in some embodiments. In other embodiments, the impeller shaft 706 may be free to rotate relative to the mounting portion 707. An optional flare portion at the distal end 711 of the impeller shaft 706 can be formed (like in FIG. 5A) to prevent the mounting portion 707 from translating in the distal direction relative to the shaft 706. The distal end 711 of the impeller shaft, which can include the flared portion, may be disposed in a recess of an enlarged distal portion of the mounting portion 707 (e.g., an interface member). As shown, a proximal portion of the mounting portion 707 can include a bushing portion disposed about the impeller shaft 706 near the proximal portion 714 of the support member 708. The flared portion of the distal end 711 of the impeller shaft 706 can have a diameter larger than the bushing portion.

A re-sealable member 754, or a septum, can be inserted within a stepped region or recess near the distal end 760 of mounting portion 707, e.g., into an enlarged portion disposed distal the enlarged portion in which the distal end 711 of the impeller shaft 706 is disposed. The re-sealable member 754 can be employed to reseal the aperture formed when the guidewire and/or guidewire guide 750 (e.g., made of stainless steel) is removed. For example, the mounting portion 707 can press against the re-sealable member 754 to compress or force the re-sealable member 754 radially inward, such that the re-sealable member 754 is pre-loaded to re-seal the lumen when the guidewire guide 750 and/or guidewire is removed. In some embodiments, the re-sealable member 754 may not rotate relative to the impeller shaft 706 and/or the mounting portion 707. In other embodiments, the re-sealable member 754 may rotate with the mounting portion 707. The re-sealable member 754 can be a self-healing polymer and/or a high durometer polymer, or any other polymer suitable for resealing the guidewire guide 750. As shown in FIGS. 7A-7B, the re-sealable member 754 can be disposed distally of the impeller shaft 706 in the stepped region or recess of a distal portion of the mounting portion 707 (e.g., an interface member). In addition, the flared portion at the distal end 711 can be disposed in or near the recess that includes the re-sealable member 754.

The nose member 709 can be installed within the distal end 760 of the mounting portion 707. Barbs within the nose member 709 can engage with slots located in the mounting portion 707. Because the nose member 709 couples to the mounting portion 707, and because the mounting portion 707 couples to the impeller shaft 706, both the nose member 709 and the mounting portion 707 can rotate with the impeller 703. The support member 708 can remain rotationally fixed, such that the support member 708 does not rotate with the impeller 703.

In the implementation of FIGS. 7A-7B, therefore, the stiff length may be reduced while also introducing a resealing member (a "septum") to prevent fluid from entering the apertures formed when the guidewire guide tube is retracted after using a guidewire with the Seldinger technique. In addition, the washer 756, which may be coupled to the proximal end of the support member 708, prevents distal axial translation of the support member 708. By securing the support member 708 in the distal direction, the distal bearing support 701 can advantageously avoid damaging the nose member 709 and/or jamming the impeller 703 due to translation of the support member 708.

Modifications of catheter pumps incorporating a catheter assembly with a distal impeller support can be used for right side support. For example, a catheter body carrying the impeller and distal bearing support can be formed to have a deployed shape corresponding to the shape of the vasculature traversed between a peripheral vascular access point and the right ventricle. One will appreciate from the description herein that the catheter assembly may be modified based on the respective anatomy to suit the desired vascular approach. For example, the catheter assembly in the insertion state may be shaped for introduction through the subclavian artery to the heart. The catheter pump may be configured for insertion through a smaller opening and with a lower average flow rate for right side support. In various embodiments, the catheter assembly is scaled up for a higher flow rate for sicker patients and/or larger patients.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump, comprising:
   a motor;
   an elongated catheter body coupled with the motor, the elongated catheter body comprising a distal portion;
   an expandable cannula disposed at the distal portion and comprising an inlet and an outlet;
   an impeller mounted on an impeller shaft coupled to the motor such that operation of the motor causes rotation of the impeller to draw blood into the expandable cannula, the impeller disposed within the expandable cannula between the inlet and the outlet, the impeller configured to be inserted into a subject while disposed within the expandable cannula; and
   an expandable distal bearing support configured to provide radial support of the impeller shaft within the expandable cannula, the expandable distal bearing support comprising a support member having:
      a proximal portion coupled to and axially overlapping a distal end of the impeller shaft, the impeller shaft configured to rotate relative to the proximal portion, and
      a lobe extending distally from the proximal portion.

2. The catheter pump of claim 1, wherein the lobe comprises distal struts configured to contact an internal wall of the expandable cannula and coupled to proximal struts, the proximal struts coupled to and extending distally from the proximal portion of the support member.

3. The catheter pump of claim 1 wherein the motor is disposed at a proximal end of the elongate catheter body, wherein the motor is configured to remain remote from the impeller and to remain outside a patient.

4. The catheter pump of claim 1 further comprising a re-sealable member disposed distally of the impeller within the expandable distal bearing support.

5. The catheter pump of claim 4, wherein the re-sealable member is coupled to the impeller shaft to enable the impeller shaft to rotate in the expandable distal bearing support, wherein the re-sealable member is held stationary with respect to the impeller shaft and distal of but aligned with the impeller.

6. The catheter pump of claim 1 further comprising a mounting portion positioned over the distal end of the impeller shaft and with which the proximal portion of the support member interfaces when the impeller shaft and mounting portion turn.

7. The catheter pump of claim 1 further comprising a nose member coupled to the impeller shaft distal of the proximal portion of the support member, the nose member configured to smooth a flow of blood to the impeller and to retain the expandable distal bearing support on the impeller shaft.

8. The catheter pump of claim 7, wherein the distal end of the impeller shaft comprises engagement features configured to secure the nose member onto the impeller shaft when engaged by the nose member.

9. The catheter pump of claim 7, wherein the proximal portion of the support member comprises a flaring at a proximal end thereof, the flaring configured to enable the proximal portion to pass proximally over the nose member during assembly.

10. The catheter pump of claim 1, wherein the expandable distal bearing support comprises first and second lobes spaced circumferentially from each other.

11. The catheter pump of claim 1 further comprising a spacer disposed between the impeller and the proximal portion of the expandable distal bearing support.

12. A catheter pump, comprising:
   a motor;
   an elongated catheter body coupled with the motor, the elongated catheter body comprising a distal portion;
   an expandable cannula disposed at the distal portion and comprising an inlet and an outlet;
   an impeller mounted on an impeller shaft coupled to the motor such that operation of the motor causes rotation of the impeller to draw blood into the expandable cannula, the impeller disposed within the expandable cannula between the inlet and the outlet, the impeller configured to be inserted into a subject while disposed within the expandable cannula; and
   an expandable distal bearing support configured to provide radial support of the impeller shaft within the expandable cannula, the expandable distal bearing support comprising a mounting portion coupled to a distal end of the impeller shaft to enable the impeller shaft to turn relative to the mounting portion, and a support member having:
      a proximal portion coupled to the mounting portion and axially displaced distally of a distal end of the impeller shaft, and
      a lobe extending distally from the proximal portion.

13. The catheter pump of claim 12, wherein the impeller shaft has an enlarged diameter at the distal end and the mounting portion has a diameter less than the enlarged diameter at a proximal end of the mounting portion.

14. The catheter pump of claim 13, wherein the mounting portion comprises an enlarged distal end having an inner diameter greater than the enlarged diameter at the distal end of the impeller shaft.

15. The catheter pump of claim 12 further comprising a re-sealable septum disposed in the mounting portion of the expandable distal bearing support.

16. The catheter pump of claim 15, further comprising a nose member coupled with a distal end of the mounting portion, the nose member having a rounded distal portion with an aperture for passage of a guidewire through the impeller and the re-sealable septum.

17. The catheter pump of claim 12, wherein the lobe comprises distal struts configured to contact an internal wall of the expandable cannula and coupled to proximal struts, the proximal struts coupled to and extending distally from the proximal portion of the support member.

18. The catheter pump of claim 12, wherein the expandable distal bearing support comprises first and second lobes spaced circumferentially from each other.

19. The catheter pump of claim 12, wherein the impeller shaft comprises a flaring at the distal end thereof.

20. The catheter pump of claim 12 further comprising a spacer disposed between the impeller and the mounting portion of the expandable distal bearing support.

* * * * *